(12) United States Patent
Sioshansi et al.

(10) Patent No.: US 6,436,026 B1
(45) Date of Patent: Aug. 20, 2002

(54) FLEXIBLE, CONTINUOUS, AXIALLY ELASTIC INTERSTITIAL BRACHYTHERAPY SOURCE

(75) Inventors: Piran Sioshansi, Lincoln; Raymond J. Bricault, Jr., West Boylston, both of MA (US)

(73) Assignee: RadioMed Corporation, Tyngsborough, MA (US)

( * ) Notice: Subject to any disclaimer, the term of this patent is extended or adjusted under 35 U.S.C. 154(b) by 0 days.

(21) Appl. No.: 09/425,126

(22) Filed: Oct. 22, 1999

(51) Int. Cl.[7] ................................................. A61M 5/00
(52) U.S. Cl. ......................................................... 600/3
(58) Field of Search ............................... 600/1, 3, 4, 7, 600/8

(56) References Cited

U.S. PATENT DOCUMENTS

| | | | |
|---|---|---|---|
| 4,702,228 A | 10/1987 | Russell, Jr. et al. ......... 128/1.2 |
| 4,754,745 A | * 7/1988 | Horowitz ........................ 600/8 |
| 4,946,435 A | 8/1990 | Suthanthiran et al. ......... 600/3 |
| 4,957,476 A | 9/1990 | Cano ................................ 600/7 |
| 5,030,195 A | 7/1991 | Nardi .............................. 600/7 |
| 5,059,166 A | 10/1991 | Fischell et al. |
| 5,176,617 A | 1/1993 | Fischell et al. ................ 600/3 |
| 5,267,960 A | * 12/1993 | Hayman et al. ............ 600/3 X |
| 5,342,283 A | 8/1994 | Good .............................. 600/8 |
| 5,395,300 A | 3/1995 | Liprie ............................ 600/3 |
| 5,405,309 A | 4/1995 | Carden, Jr. ..................... 600/3 |
| 5,411,466 A | 5/1995 | Hess ............................... 600/3 |
| 5,498,227 A | 3/1996 | Mawad ........................... 600/3 |
| 5,503,614 A | 4/1996 | Liprie ............................ 600/7 |
| 5,575,749 A | 11/1996 | Liprie ............................ 600/3 |
| 5,607,442 A | 3/1997 | Fischell et al. ................ 600/3 |
| 5,624,372 A | 4/1997 | Liprie ............................ 600/3 |
| 5,637,073 A | 6/1997 | Freire ............................ 600/3 |
| 5,722,984 A | 3/1998 | Fischell et al. ............. 606/198 |
| 5,840,009 A | 11/1998 | Fischell et al. ................ 600/3 |
| 5,857,956 A | * 1/1999 | Liprie ............................ 600/7 |
| 5,924,974 A | * 7/1999 | Loffler ........................... 600/3 |
| 6,152,869 A | * 11/2000 | Park et al. ..................... 600/3 |

FOREIGN PATENT DOCUMENTS

| | | |
|---|---|---|
| SU | 799 189 | 8/1983 |
| WO | WO 99/33063 | 7/1999 |

OTHER PUBLICATIONS

Blasko, "Long–Term Outcomes Of External Beam Irradiation And 1–25/:Pd–103 Brachytherapy Boost For Prostate Cancer", *I. J. Radiation Oncology·Biology·Physics*, vol. 36, No. 1, Supplemental 1996.

Dattoli et al., "$^{103}$Pd Brachytherapy and External Beam Irradiation For Clinically Localized, High–Risk Prostatic Carcinoma", *Int. J. Radiation Oncology Biol. Phys.*, vol. 35, No. 5, pp. 875–879, 1996.

Finger et al., "Palladium 103 Ophthalmic Plaque Radiotherapy", *Arch Ophthalmol*, vol. 109, pp. 1610–1613, 1991.

Finger et al., "Palladium–103 Versus Iodine–125 For Ophthalmic Plaque Radiotherapy", *Int. J. Radiation Oncology Biol. Phys.*, vol. 27, No. 4, pp. 849–854, 1993.

(List continued on next page.)

*Primary Examiner*—John P. Lacyk
*Assistant Examiner*—Joseph H Cadugan
(74) *Attorney, Agent, or Firm*—McDermott, Will & Emery

(57) ABSTRACT

A flexible, continuous, axially elastic interstitial brachytherapy source is capable of elongating, shrinking and/or flexing in response to changes in the size and/or shape of a tumor, tumor bed, lesion or other tissue with which the source is in contact. In one embodiment, the source is in the form of a wire coil. The flexible and expandable/contractible nature of the source allows it to provide therapeutically effective treatment to dynamic tissue as it swells, shrinks and/or changes in shape.

5 Claims, 3 Drawing Sheets

OTHER PUBLICATIONS

Fix, PD–103 Seeds Treat Intraocular Tumors With Less Radiation Exposure To Healthy Tissue, *Advance For Administrators in Radiology*, p. 47, Sep. 1994.

Guttman, "Interstitial Brachytherapy Making Comeback", *Urology Times*, Oct. 1993.

Prestidge et al., "Post–Treatment Biopsy Results Following Interstitial Brachytherapy In Early Stage Prostate Cancer", 37th Annual Scientific Meeting of the American Society For Therapeutic Radiology and Oncology, Miami Beach, Florida, Oct. 9, 1995.

Ragde, "Brachytherapy (Seed Implantation) for Clinically Localized Prostate Cancer", *J. Surg. Oncol.*, vol. 64, pp. 79–81, 1997.

Ragde et al., "Brachytherapy In The Management Of Clinically Organ–Confined Prostate Cancer", First International Consultation on Prostate Cancer, World Health Organization, Monacao, Jun. 20–22, 1996, pp. 1–12.

Skerrett, "Radioactive Pellets Speed Prostate Recovery", *Medical World News*, Jan. 1994.

Skolnick, "Radiation Therapy For "Wet" Type Macular Degeneration Shows Promise In Early Trials", *JAMA*, vol. 277(9) 1997.

"Therapeutic Options Available For Testing Prostate Cancer", *The BBI Newsletter*, vol. 19, No. 4, pp. 72–74, Apr. 1996.

"TheraSeed™ Palladium 103 Implants", *Theragents Corporation*, May 31, 1990.

"Beta Radiation May Stop Wet Macular Degeneration", *eyesotopes*, The International Newsletter For Eye Tumor Experts, No. 5, Apr. 1997.

"Ru–106 Opthalmic Plaques", from Germany, *BEBIG*.

Eigler et al., "A $^{48}$Vanadium Brachytherapy Source for Treatment of Coronary Artery Restenosis", *Vascular Brachytherapy*, Chapter 23, pp. 231–236, 1996.

* cited by examiner

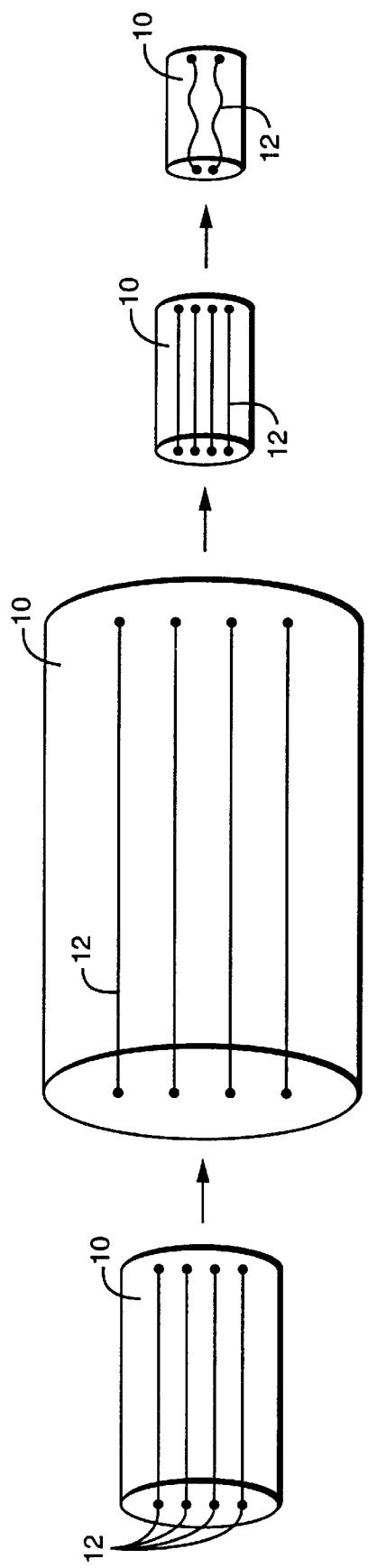

FLEXIBLE, CONTINUOUS, AXIALLY ELASTIC INTERSTITIAL BRACHYTHERAPY SOURCE

TECHNICAL FIELD

The present invention relates to interstitial brachytherapy sources for use in the treatment of tumors, cancers and other proliferative tissue.

BACKGROUND OF THE INVENTION

Brachytherapy is the science of applying radioactivity to living tissue over relatively short distances in order to retard cell growth or induce cell death in a targeted area. When cancerous and other proliferative tissues are to be treated, it is desirable to target the radiation therapy with a high degree of specificity to avoid damaging irradiation of surrounding healthy tissue.

External radiotherapy systems administer radiation in a directed beam. Even when the tissue to be treated falls within a therapeutically active depth for a given beam energy, the intervening and surrounding healthy tissue is irradiated needlessly.

Interstitial brachytherapy sources allow radiation to be targeted more specifically and more deeply in living tissue. The use of radioactive seeds in the treatment of prostate tumors is one example of an interstitial brachytherapy source. Such seeds are usually loaded into a delivery vehicle which is then removed from the tissue after the seeds are implanted.

One disadvantage of brachytherapy seeds is that they are discrete, or "point", sources of radiation and thus do not provide a continuous or uniform dosage over any length of treatment area. To provide a semblance of dosage continuity, seeds would need to be closely and uniformly spaced, and this is difficult and time consuming, without reliable assurances that the seeds will remain as placed. Because the seeds can migrate in the tissue, they may become either too closely spaced or too far apart, which further detracts from optimal dosage delivery. Thus, they cannot reliably assure a constant or uniform dosage to the targeted tissue, and they may cause unnecessary radiation damage to surrounding healthy tissue.

Further complicating the application of interstitial brachytherapy is the fact that while a particular radiation distribution may be preferred based on the treated volume prior to implantation of the source, the tissue constituting the volume to be treated changes shape and size (as, for example, enlarging and swelling caused by localized edema due to the trauma of the insertion of the source, and shrinking due to subsequent radiation treatment of the tissue). Such changes in the shape and size of the tissue can change the preferred radiation distribution. However, current brachytherapy sources are not believed to adequately address this problem.

For example, many tumors, tumor beds and lesions are effectively treated with radiation administered from an interstitial brachytherapy source in the form of radioactive wires, rods or ribbons. However, these sources are in fact packages of seeds which are held together inside a catheter, sheath, tube or the like. Further, even in such "extended" sources, the activity is present at discrete locations along the length of the source instead of continuously along the length of the source. This produces an inferior dose distribution and may create an unacceptably high contact dose in the active regions in which the source is located. One consequence of this is the possibility that such treatment could produce cosmetic damage, such as dimpling or holes, in tissues such as that of the breast. In addition, these extended sources are not continuously flexible. Rather, they are flexible only between the seeds and rigid in the areas at which the seeds are located. Rods are clearly not flexible, and even the wires and ribbons are made from heavy-gauge stock which is not flexible. Finally, none of these extended sources is extendible in the axial direction, nor are they designed for axial expansion. Rods and wires would break if axially expanded, and ribbons, if bent or stretched, would lose their characteristic source-to-source spacing. Thus, all of the prior art sources are inadequate in adapting to the changing size and shape of the treated tissue.

Stents have also recently been promoted for brachytherapy treatments. Radioactive stents act as devices which radially expand into place when inserted into a lumen at a treatment site and deliver radiation to maintain the patency of the lumen and prevent restenosis. A stent, once deployed, is typically relatively stiff in the radial direction so as to support the surrounding tissue to prevent restenosis, and also relatively stiff in the axial direction so as to resist being dislodged from its initial position.

The goal of stent brachytherapy is to inhibit or retard localized regrowth of cells and the acquisition or deposition of extracellular media on the inner surface of the vessel. A typical radioactive intensity for a radioactive stent is in the neighborhood of about 1 to 20 microCuries, so as to deliver a nominal radiation dosage to a surrounding vessel of about 15 Gy at a distance of about 1 mm from the surface of the stent. A total volume of tissue to be treated with a radioactive stent is typically about 0.4 mm$^3$.

The effective treatment of tumorous tissue, on the other hand, requires that all cells in the affected region be ultimately eradicated. It is reported that if even 30 cancerous cells per cubic millimeter survive a cancer therapy, the cancer can regrow at that location. As an example, brachytherapy seeds typically have an activity of about 1.4 milliCuries per seed, and nominally one hundred seeds are used to treat, for example, a prostate cancer, for a total activity of about 140 milliCuries. The typical prescribed dose is in the range of 80 to 200 Gy, and for palladium-103, commonly used in prostate tumor therapy, it is about 115 Gy. Seeds are typically spaced 1 cm apart, although uniform seed spacing and uniform dosages cannot be assured. A total volume of tissue to be treated with seeds is typically about 60 cm$^3$.

The dosages and activities required for effective tumor treatment are much higher than for stenosis prevention. Such dosages and activities are not typically provided with radioactive stents.

Therefore, the effectiveness of prior art interstitial brachytherapy sources and devices such as stents is limited in tumorous and other proliferative tissue which may undergo changes in size and shape during therapy.

It is therefore an object of the invention to provide an interstitial brachytherapy source which can shrink and grow in response to changes in the size and shape of tissue with which the source is in contact. In particular, it is an object of the invention to provide a flexible, continuous, axially elastic interstitial brachytherapy source.

SUMMARY OF THE INVENTION

The invention comprises, in one aspect, an interstitial radioactive implant, or source, which is capable of changing its shape and/or size in substantially all directions in response to changes in the shape and/or size of tissue with which the implant is in contact. In a preferred embodiment, the radioactive implant defines a substantially continuous source of radiation that extends along a principal axis. If the tissue behavior warrants, the source is capable of expanding and contracting in the direction of the principal axis, as well as flexing in directions other than the principal axis.

In one embodiment, the radioactive source comprises a wire in the form of a coil. The diameter of the wire is preferably between about 10 and about 250 micrometers. The outer diameter of the coil is preferably between about 25 and about 1500 micrometers.

In a preferred embodiment, the radioactive wire coil has a specific activity of at least 10 microCuries/cm. A preferred range of specific activity is between about 100 microCuries/cm and about 50 milliCuries/cm.

The coil may be manufactured to virtually any length and then cut to a length which is appropriate for treatment of the lesion, tumor or cancer of interest.

The source may include tissue anchors at opposite ends thereof and/or at intermediate points to fix the source in the tissue to be treated.

These and other objects and advantages of the invention will in part be obvious and will in part appear hereinafter. The invention accordingly comprises the apparatus possessing the construction, combination of elements and arrangement of parts which are exemplified in the following detailed disclosure, the scope of which will be indicated in the claims.

BRIEF DESCRIPTION OF THE DRAWINGS

For a fuller understanding of the nature and objects of the present invention, reference should be had to the following detailed description taken in connection with the accompanying drawings, in which:

FIGS. 1A–1D are simplified schematic diagrams of the axially elastic nature of the source according to the invention, as implanted in living tissue;

Like elements in the FIGURES are indicated by like reference numerals.

DETAILED DESCRIPTION OF THE DRAWINGS

The interstitial brachytherapy source of the present invention comprises, in its simplest form, a flexible, continuous, axially elastic radioactive implant which is capable of extending and contracting in length, as well as bending or flexing, in response to changes in the size and/or shape of the tissue with which it is in contact. In one preferred form, the source is a wire that has been formed into a coil. Other axially elastic structures, such as a telescoping structure or an elastic member, are also considered to be within the scope of the invention.

The term "interstitial", as used herein, means that the source is used principally within or proximate to living proliferative tissue, such as cancers, tumor beds, tumors (malignant or benign), and other proliferative lesions. The term "axially elastic", as used herein, means that the source is capable of lengthening and shortening in the direction of a principal axis in response to some physical force exerted on the source. The term "continuous", as used herein, means that the source is radioactive along substantially its entire length, as opposed to having discrete points of radioactivity, such as is characteristic of brachytherapy seeds or seeded ribbons, wires or rods.

FIGS. 1A–1C illustrate the concept of an axially elastic interstitial implant in tissue 10 to be treated with radiation, such as a tumor, in order to reduce its size. Several implants 12 are implanted into the tissue 10 as shown in FIG. 1A, typically in a parallel arrangement. Immediately following implantation of the sources, the tissue 10 responds to the trauma of introduction of the insertion needle by swelling and expands in size, as shown in FIG. 1B. The swelling response is temporary, and the tissue returns to its nominal size in a relatively short time following implantation of the sources. Thereafter, as shown in FIG. 1C, the tissue 10 may shrink in response to the dosage of radioactivity delivered by the implants 12. The implants 12 of the invention can expand and contract with swelling and shrinkage of the tissue, thereby retaining their orientation to one another and their relative positions within the tissue.

It is preferred that the source also be generally relatively flexible, so that it can bend and curve in directions other than the principal axis in response to changes in the shape of the tissue with which it is contact.

Figure 3:
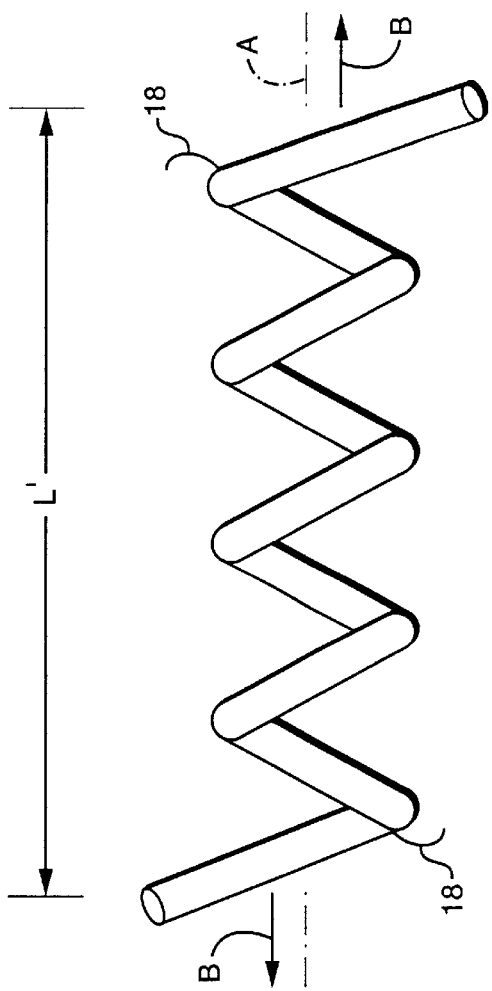
FIG. 3 is a side view of the coiled wire embodiment of FIG. 2 in an expanded state.
Figure 2:
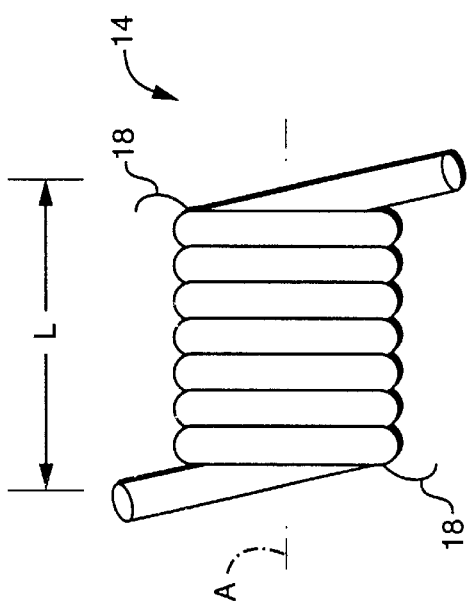
FIG. 2 is a side view of one embodiment of the source, a coiled wire, in a relaxed, fully contracted state.
Figure 4A:
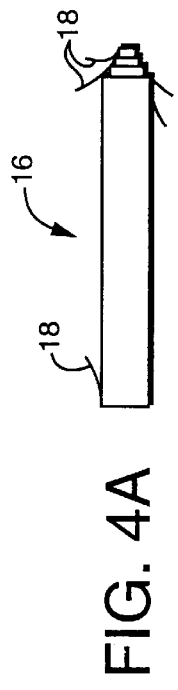
FIGS. 4A–4D are side views of a different embodiment of the source, an axially telescoping structure, in progressively expanded states.
Figure 4B:
Figure 4C:
Figure 4D:

One preferred embodiment of the source, in the form of a coiled wire 14, is shown in FIGS. 2 and 3. FIG. 2 shows a coiled wire in a nominally relaxed state which, in this instance, is represented by a fully compacted coil extending along a principal axis A for a nominal length L. At least one end, and preferably both ends, of the coil may extend beyond the nominal coil diameter as relatively straight extensions of the wire at the ends of the coil.

FIG. 3 illustrates the coiled wire of FIG. 2 which has been extended to a length L' greater than L in response to opposing outward (tensile) forces on the coil, indicated by arrows B in FIG. 3. The coiled design of the implant ensures that it will engage with the tissue, and thus move with the tissue. The coiled design also ensures that the implant is sufficiently flexible to bend as the tissue changes in shape and/or size following implantation and during therapy. Other features of the coiled design include a natural kink-resistance and a characteristic stiffness which determines, in part, its elasticity and ability to elongate and contract in response to the forces of tissue around the source.

The coil may be implanted in a contracted, relatively compact state into a tumor or tumor bed by, for example, inserting a supporting mandrel into the coil, or placing the coil in a housing, such as a needle, injecting the coil and mandrel or housing into the tissue, and withdrawing the mandrel or housing so as to leave the coil in place in the tissue, as in FIG. 1A. Swelling of the tissue after implantation may cause the coil engaged by the tissue to expand from its nominal contracted state, illustrated in FIGS. 1B and 3. Subsequent shrinkage of the tissue may cause the coil to contract, as illustrated in FIG. 1C. As the tissue continues to shrink, the coil may also bend or flex in directions other than the principal axis of the coil, as shown in FIG. 1D.

The diameter of the wire forming the coil is preferably between about 10 and about 250 micrometers. The outer diameter of the coil is preferably between about 25 and about 1500 micrometers. Much smaller than a typical stent, the coil of the invention is used interstitially, i.e., within relatively dense tissue, such as tumors, rather than in a lumen or vessel. The principal function of the source of the invention is to impart a continuous and flexible source of radiation which is also elastic in the direction of its principal axis, so that it can grow and shrink with the tissue being treated and thus remain effective for the duration of treatment.

FIGS. 4A–4D illustrate another embodiment of the source of the invention. The source is in the form of an axially telescoping structure 16 which extends in the direction of a principal axis A. The telescoping structure may include several tubular portions of diminishing diameter.

Figure 5A:
FIGS. 5A–5B are side views of still another embodiment of an axially elastic structure, in contracted and expanded states.
Figure 5B:
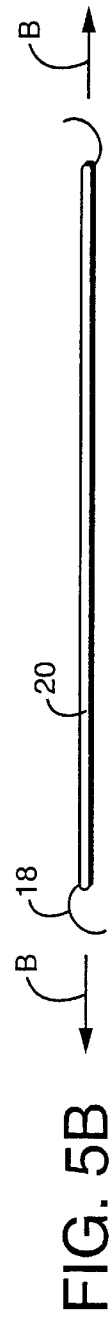

FIGS. 5A–5B illustrate another embodiment of the source, in the form of a substantially axially elastic wire or rod 20. This source operates in the same fashion as the telescoping structure and the coil. Swelling or shrinkage of the tissue allows the source to stretch or shrink with the tissue.

Both structures are preferably constructed to define a continuous source of radiation which can be extended or shortened in the direction of the principal axis of the source.

As shown in FIGS. 2, 3 and 4A–4D, the sources may include tissue anchors 18 at end portions or intermediate portions thereof. The tissue anchor may be in the form of a barb, hook or other tissue-engaging structure which anchors a portion of the implant in surrounding tissue. When the tissue swells or shrinks, the anchors engage with the surrounding tissue and allow the implant to elongate or retract axially in response to such swelling or shrinking.

Any therapeutically effective radioisotope can be associated with the sources of the invention, in any way which allows the source to become radioactive over at least a portion of its length. Some known methods of radioisotope incorporation include, for example, ion implantation of a radioisotope into the material of the source, plating, chemical and vapor deposition processes (including various forms of ion beam and plasma-based sputtering,, evaporation, and laser ablation), cathodic arc plasma deposition, ion plating, thermal spray, plasma spray, and flame spray, and nuclear transmutation and neutron activation of a nonradioactive species into a radioactive species.

There are numerous advantages to an interstitial implant which can grow, flex and shrink with the tissue to be treated. First, it is possible to precisely localize the implants in and near the tissue to be treated, with a high reliability that the implants will remain in the desired relative orientations and positions during the treatment period. Second, the risk of migration of the radioactive implants as the tissue grows and shrinks, and over- and under-dosage that results from migration, is minimized or eliminated. An even dose distribution is assured. Third, the implants focus radiation specifically on tissue to be treated, with less irradiation to surrounding healthy tissue and organs. Fourth, the flexible nature of the implants allows them to match the contour of a tumor, lesion or tumor bed, resulting in less trauma, less edema, promotion of healing, less scarring, and less discomfort to the patient.

The implant of the invention defines a flexible and substantially continuous radiation source, in contrast to radioactive seeds, which define rigid and discrete point sources of radiation. The continuous nature of the radiation provides a relatively even dosage along the length of the source and thus allows the source to be used to treat greater volumes of tissue with a more uniform radiation dose.

Two applications of particular interest for the source of the invention are the treatment of tumors of the prostate gland and of the breast. In prostate gland brachytherapy, it is desirable to implant several fine coiled wires in a parallel arrangement in and through the proliferative tissue within the prostate. The wire coil preferably has a specific activity of between about 0.1 milliCurie/cm and about 5 milliCuries/cm, with a preferred target specific activity of about 1.4 milliCuries/cm.

For treatment of breast tumors, a preferred subrange of specific activity for the implant is between about 0.1 milliCurie/cm and about 10 milliCuries/cm. A preferred target specific activity for breast tissue brachytherapy is about 5 milliCuries/cm. Breast brachytherapy sources may be used alone or with other radiation therapies.

The following non-limiting examples are presented.

Example I

Prostate Tumor Brachytherapy

A wire made of rhodium and having a diameter of 100 micrometers is formed into a coil having an outer diameter of about 850 micrometers. The coil is densely wound, with no spacing between individual adjacent windings. The coil is then activated by proton bombardment so as to transmute the rhodium to palladium- 103 having an activity of 3 milliCurie/cm. The coil is formed to between 1 and 8 cm in length and is radioactive along its full length.

Example II

Breast Tumor Brachytherapy

A wire made of tantalum and having a diameter of 25 micrometers is activated by sputtering the radioisotope iridium-192 onto it. The wire is then formed into a coil having an outer diameter of about 1000 mm. The coil, as formed, has an activity of 6 milliCurie/cm. The coil is formed to between 4 and 20 cm in length and is radioactive along its length except for the two ends of the coil.

The coiled sources formed according to the invention are axially elastic and are thus capable of elongation and contraction in the direction of their principal axes. They are also capable of flexing in directions other than the direction of the principal axis of the coil.

Because certain changes may be made in the above source without departing from the scope of the invention herein disclosed, it is intended that all matter contained in the above description or shown in the accompanying drawings shall be interpreted in an illustrative and not a limiting sense.

We claim:

1. An interstitial brachytherapy source, comprising a radioactive implant that can change its size in response to changes in the size of tissue with which the implant is in contact, wherein the radioactive implant defines a substantially continuous source of radiation which extends along a principal axis, wherein the implant that is expandable and contractable in the direction of said principal axis, and wherein the radioactive implant comprises a wire in the form of a coil.

2. An interstitial brachytherapy source according to claim 1, wherein the diameter of the wire is between about 10 and about 250 micrometers, and wherein the outer diameter of the coil is between about 25 and about 1500 micrometers.

3. An interstitial brachytherapy source according to claim 1, wherein the implant comprises an axially elastic structure.

4. An interstitial brachytherapy source according to claim 1, wherein the implant comprises an axially telescoping structure.

5. An interstitial brachytherapy source according to claim 1, wherein the implant includes one or more tissue anchors.

* * * * *